US008105600B2

(12) United States Patent
Koff et al.

(10) Patent No.: US 8,105,600 B2
(45) Date of Patent: Jan. 31, 2012

(54) METHOD OF INDUCING HIGH-TITER NEUTRALIZING ANTIBODY RESPONSES IN A HOST BY ADMINISTERING IMMUNE COMPLEXES COMPRISING ANTI-HIV-1 ENV ANTIBODIES AND THE HIV-1 ENV

(75) Inventors: Wayne C. Koff, Stony Brook, NY (US); Sanjay Phogat, Frederick, MD (US)

(73) Assignee: International Aids Vaccine Initiative, New York, NY (US)

( * ) Notice: Subject to any disclaimer, the term of this patent is extended or adjusted under 35 U.S.C. 154(b) by 22 days.

(21) Appl. No.: 12/261,359

(22) Filed: Oct. 30, 2008

(65) Prior Publication Data

US 2009/0123485 A1 May 14, 2009

Related U.S. Application Data

(63) Continuation-in-part of application No. 11/929,015, filed on Oct. 30, 2007, now abandoned, and a continuation-in-part of application No. PCT/US2007/083006, filed on Oct. 30, 2007.

(60) Provisional application No. 60/855,625, filed on Oct. 30, 2006, provisional application No. 61/035,653, filed on Mar. 11, 2008.

(51) Int. Cl.
*A61K 39/00* (2006.01)
*A61K 39/21* (2006.01)
*A61K 39/42* (2006.01)

(52) U.S. Cl. ................ 424/178.1; 424/160.1; 424/208.1

(58) Field of Classification Search ........................ None
See application file for complete search history.

(56) References Cited

U.S. PATENT DOCUMENTS 6,676,958 B2 1/2004 Gerber

FOREIGN PATENT DOCUMENTS

WO WO 2006 112929 10/2006
WO WO 2006/112929 A2 10/2006
WO WO 2007 030518 3/2007
WO WO 2007/030518 A2 3/2007

OTHER PUBLICATIONS

Burton, D. R., et al., 2004, HIV vaccine design and the neutralizing antibody problem, Nat. Immunol. 5(3):233-236.*

Wang, L.-X., 2003, Bioorganic approaches toward HIV vaccine design, Curr. Pharm. Design 9:1771-1787.*

Walker, B. D., and D. R. Burton, 2008, Toward an AIDS vaccine, Science 320:760-764.*

Montefiori, D. C., 2005, Neutralizing antibodies take a swipe at HIV in vivo, Nat. Med. 11(6):593-594.*

Liao, H.-X., et al., 2004, Immunogenicity of constrained monoclonal antibody A32-human immunodeficiency virus (HIV) Env gp120 complexes compared to that of recombinant HIV type 1 gp120 envelope glycoproteins, J. Virol. 78(10):5270-5278.*

Pantophlet, R., et al., 2008, Neutralizing activity of antibodies to the V3 loop region of HIV-1 gp120 relative to their epitope specificity, Virol. 381:251-260.*

Yari, thesis, *Expression of anti-HIV-1 Ab in Bacteria and Eukaryotic Cells*, Karolinska Institut, Jan. 25, 2007, p. 25, paral, p. 26, para 2, p. 34, para 1, p. 34, fig 16 caption.

Gorny, et al., *Identification of a New Quaternary Neutralizing Epitope on Human 15 Immunodeficiency Virus Type 1 Virus Particles*, J Virol (2005) vol. 79, No. 8, pp. 5232-5237.

Karolinska Institute for Yari '*Expression of recombinant neutralizing anti-HIV-1 antibodies in-bacteria and eukaryotic cells*' Jan. 25, 2007. Included in support of the public disclosure of Yari on Jan. 25, 2007. Downloaded from http://diss.kib.ki.se/2oo7/978-91-7357-079-4/ on Feb. 13, 2009.

Yari, thesis, Expression of anti-HIV-1 Ab in Bacteria and Eukaryotic Cells, Karolinska Institut, Jan. 25, 2007, http://diss.kib.ki.se/2007/978-91-7357-079-4/thesis.pdf, p. 25.

Gorny, et al., Identification of a New Quaternary Neutralizing Epitope on Human Immunodeficiency Virus Type 1 Virus Particles, J Virol (2005) vol. 79, No. 8, p. 5232?5237, p. 5236.

Citation: Karolinska Institute for Yari "Expression of recombinant neutralizing anti-HIV-1 antibodies in bacteria and eukaryotic cells" Jan. 25, 2007. Included in support of the public disclosure of Yari on Jan. 15, 2007. Downloaded from http://diss.kib.ki.se/2007/978-91-7357-079-4/ on Feb. 13, 2009.

* cited by examiner

*Primary Examiner* — Jeffrey S. Parkin

(74) *Attorney, Agent, or Firm* — Thomas J. Kowalski; Deborah L. Lu; Vedder Price PC

(57) ABSTRACT

The present relation relates to antigen-antibody complexes for use as prophylactic and therapeutic vaccines for infectious diseases of AIDS. The present invention encompasses the preparation and purification of immunogenic antibody-antigen complexes which are formulated into the vaccines of the present invention.

8 Claims, 10 Drawing Sheets

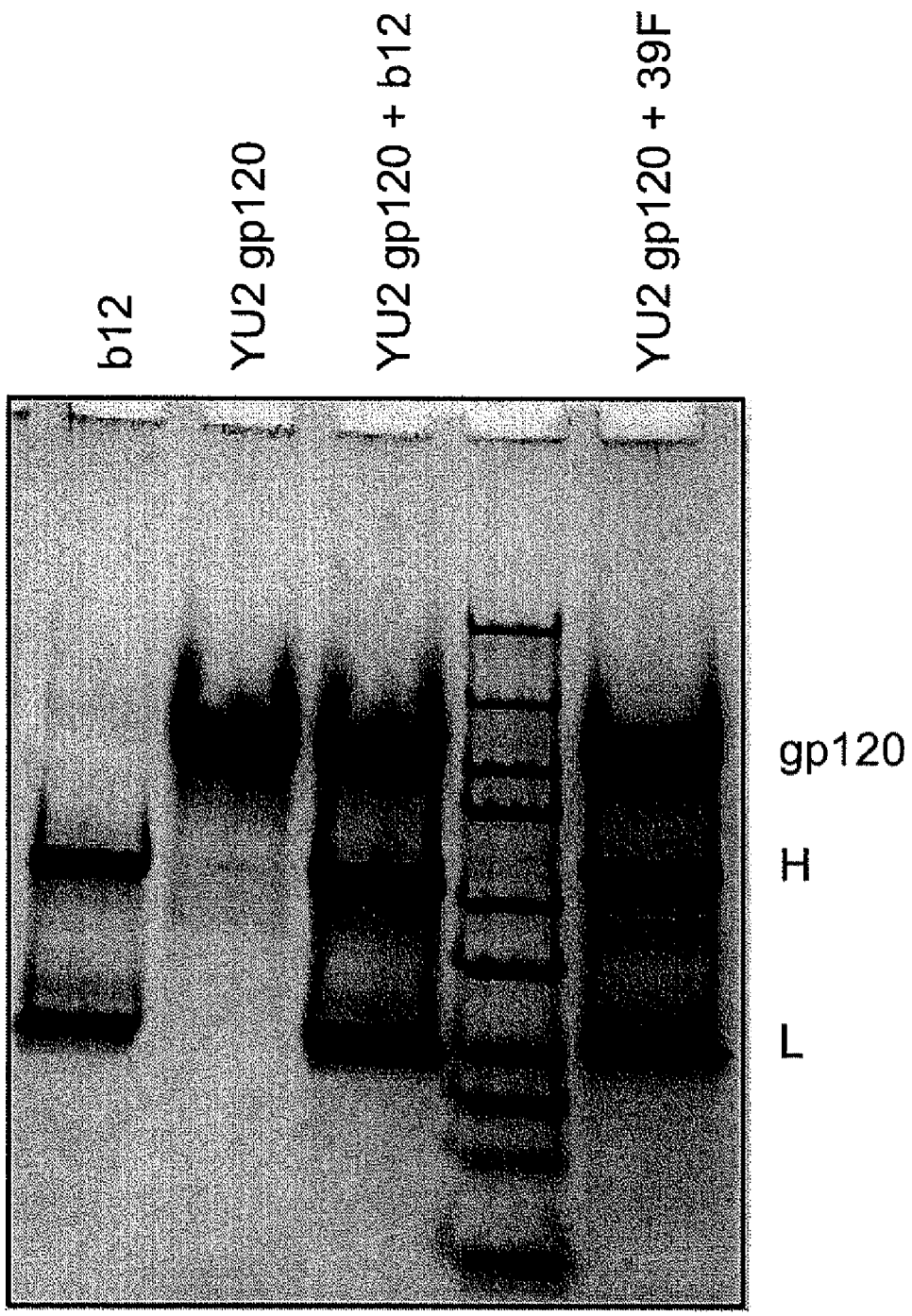
F I G. 3

*Anti-JRCSF gp120 titer

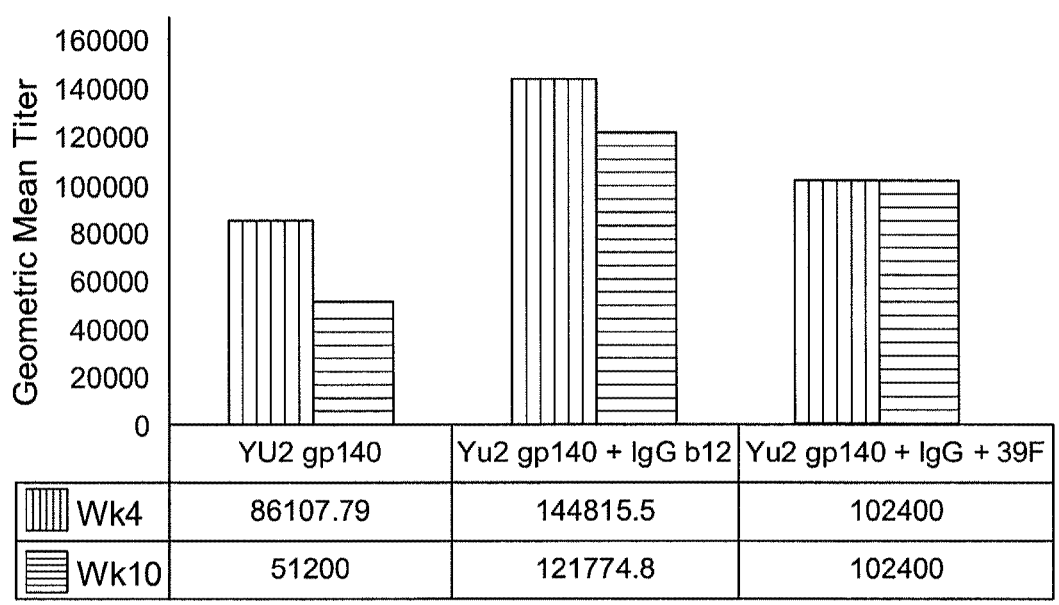
F I G. 10

METHOD OF INDUCING HIGH-TITER NEUTRALIZING ANTIBODY RESPONSES IN A HOST BY ADMINISTERING IMMUNE COMPLEXES COMPRISING ANTI-HIV-1 ENV ANTIBODIES AND THE HIV-1 ENV

INCORPORATION BY REFERENCE

This application is a continuation in part of U.S. non-provisional application Ser. No. 11/929,015 filed on 30 Oct. 2007 now abandoned and PCT International Application No. PCT/US2007/083006 filed on 30 Oct. 2007, which claims priority to U.S. provisional application Ser. No. 60/855,625, filed on 30 Oct. 2006. This application also claims priority to U.S. provisional application Ser. No. 61/035,653, filed on 11 Mar. 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to antigen-antibody complexes for use as prophylactic and therapeutic vaccines for infectious diseases of AIDS.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The Gag gene encodes core structural proteins of the nucleocapsid core and matrix. The Pol gene encodes reverse transcriptase (RT), integrase (Int), and viral protease enzymes required for viral replication. The that gene encodes a protein that is required for elongation of viral transcripts. The rev gene encodes a protein that promotes the nuclear export of incompletely spliced or unspliced viral RNAs. The Vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The Env gene encodes the viral envelope glycoprotein that is translated as a 160-kilodalton (kDa) precursor (gp160) and cleaved by a cellular protease to yield the external 120-kDa envelope glycoprotein (gp 120) and the transmembrane 41-kDa envelope glycoprotein (gp41), which are required for the infection of cells (Abbas, pp. 454-456). Gp 140 is a modified form of the env glycoprotein which contains the external 120-kDa envelope glycoprotein portion and a part of the gp41 portion of env and has characteristics of both gp 120 and gp41. The Nef gene is conserved among primate lentiviruses and is one of the first viral genes that is transcribed following infection. In vitro, several functions have been described, including down regulation of CD4 and MHC class I surface expression, altered T-cell signaling and activation, and enhanced viral infectivity.

HIV infection initiates with gp 120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp 120 expressed on the surface of infected cells. In this case, the uninfected cells bind, via the CD4 receptor-gp 120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoproteins have shown that the virus has many effective protective mechanisms with few vulnerabilities (Wyatt & Sodroski, Science. 1998 June 19;280(5371):1884-8). For fusion with its target cells, HIV-1 uses a trimeric Env complex containing gp 120 and gp41 subunits (Burton et al., Nat Immunol. 2004 March;5(3):233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events or by binding after virion attachment and inhibiting the fusion process (Parren & Burton, Adv Immunol. 2001;77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002;53:499-518).

There remains a need to identify immunogens that elicit broadly neutralizing antibodies. Strategies include producing molecules that mimic the mature trimer on the virion surface, producing Env molecules engineered to better present neutralizing antibody epitopes than wild-type molecules, generating stable intermediates of the entry process to expose conserved epitopes to which antibodies could gain access during entry and producing epitope mimics of the broadly neutralizing monoclonal antibodies determined from structural studies of the antibody-antigen complexes (Burton et al., Nat Immunol. 2004 March;5(3):233-6). However, none of these approaches have yet efficiently elicited neutralizing antibodies with broad specificity.

Citation or identification of any document in this application is not an admission that such document is available as prior art to the present application.

SUMMARY OF THE INVENTION

The current invention is based, in part, on Applicant's discovery that immunization with antigen-antibody complexes elicit neutralizing antibody responses. Broadly neutralizing antibodies, if passively administered to monkeys, protect against an HIV equivalent virus (SIV/HIV chimera, e.g., SHIV). The identification of antigens that bind the neutralizing antibodies remains challenging, especially elucidating the preferred conformation of the antigen.

The solution proposed by the present invention is immunization with the antibody-antigen complex, wherein the antigen is held in its preferred conformation by the antibody or its equivalent polyclonal sera. One of skill in the art would not expect this approach to work as the antigen are bound to the antibody and the epitopes are covered. Without being bound by theory, it is hypothesized that an antibody-antigen complex is presented to the immune system in a novel form, is dissociated within the antigen presenting cells and elicits the correct antibody response.

In an advantageous embodiment, the antigen-antibody complex is an envelope protein (such as, but not limited to, gp 120, gp 140 or membrane-associated envelope trimers) complexed with a CD4 binding site broad neutralizing antibody (such as, but not limited to, b12, 2F5), a variable loop 3 specific antibody (such as, but not limited to, 39F), a trimer-specific antibody (such as, but not limited to 2909, if the antigen is a envelope trimer protein) or a CD4 induced epitope specific antibody.

The present invention encompasses identification of antibody-antigen complexes for use as a HIV vaccine. In one embodiment, the invention relates to the identification of immunogenic antibody-antigen complexes.

In one embodiment, mixing polyclonal anti-HIV sera which demonstrate broad neutralizing activity with purified HIV enables the antibodies to bind to the glycoprotein spikes on the viral envelopes. The antibody-antigen complexes are dissociated, advantageously chemically dissociated, from the virus. The antibody-antigen complexes are purified and formulated into the vaccines of the present invention.

In another embodiment, broadly neutralizing HIV monoclonal antibodies such as, but not limited to, b12, 2F5, 2G12, 4E10, M2909 either alone or combination, are mixed with purified HIV enables the antibodies to bind the glycoprotein spikes on the viral envelopes. The antibody-antigen complexes may be dissociated, advantageously chemically dissociated, from the virus. The antibody-antigen complexes may be purified and formulated into the vaccines of the present invention.

In yet another embodiment, new broadly neutralizing antibodies to HIV are identified and mixed with purified HIV enables the antibodies to bind the glycoprotein spikes on the viral envelopes. The antibody-antigen complexes are dissociated, advantageously chemically dissociated, from the virus. The antibody-antigen complexes are purified and formulated into the vaccines of the present invention.

In still another embodiment, the antibody-antigen complexes may be identified from alternate viral isolates, such as different HIV clades. In this embodiment, polyclonal anti-HIV sera, broadly neutralizing HIV monoclonal antibodies such as, but not limited to, b 12, 2F5, 2G12, 4E10, M2909 either alone or combination, or newly identified broadly neutralizing antibodies to HIV are mixed with different HIV lade viral isolates to enable the antibodies to bind to varying antigens, thereby forming antibody-antigen complexes. The antibody-antigen complexes are dissociated, advantageously chemically dissociated, from the virus. The antibody-antigen complexes are purified and formulated into the vaccines of the present invention.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 3 depicts gel-filtration purified complexes on reducing SDS-PAGE where lane 1 is b12, lane 2 is YU2 gp 120, lane 3 is YU2 gp 120 +b12 and lane 4 is YU2 gp 120+39F.

FIG. 10 depicts an antibody response to YU2 gp 140 immune complex after immunization in rabbits at weeks 4 and 10.

DETAILED DESCRIPTION

Figure 1:
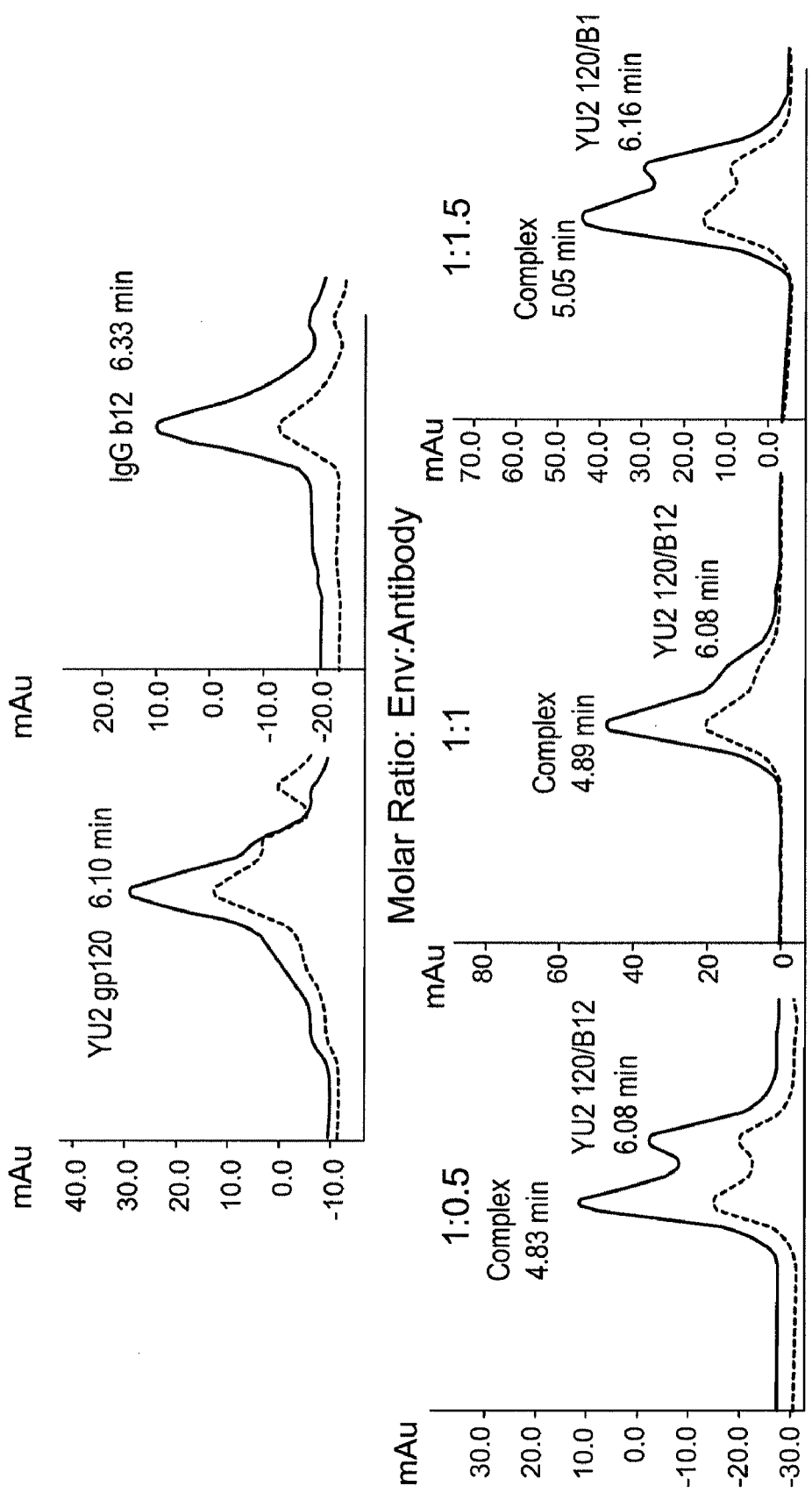
FIG. 1 depicts immune complexes of YU2 gp 120-B12 run on a gel filtration column.
Figure 2:
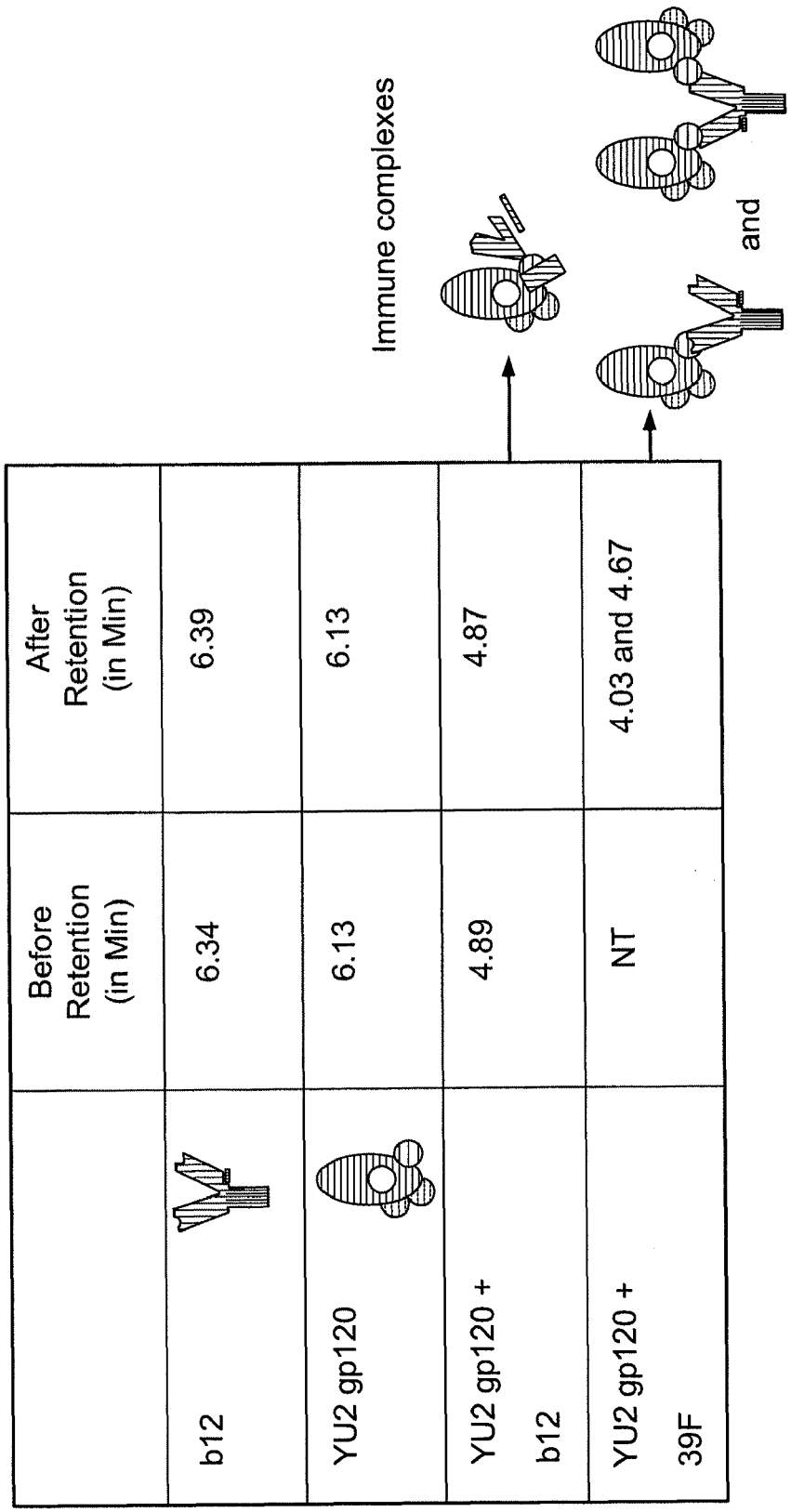
FIG. 2 depicts an analysis of immune complexes before and after gel filtration.
Figure 4:
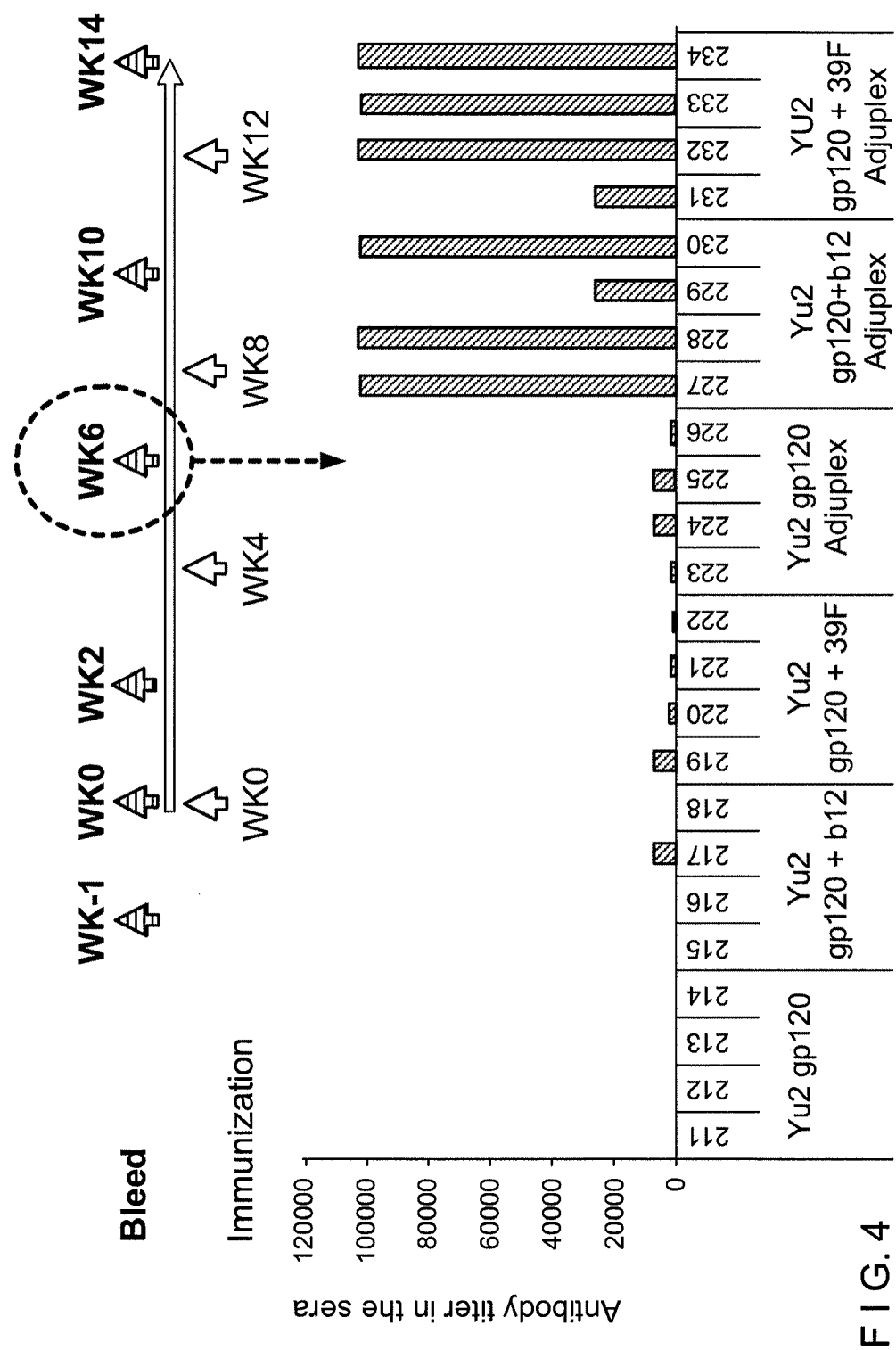
FIG. 4 depicts an antibody response to immune-complex by single prime-boost immunization.
Figure 5:
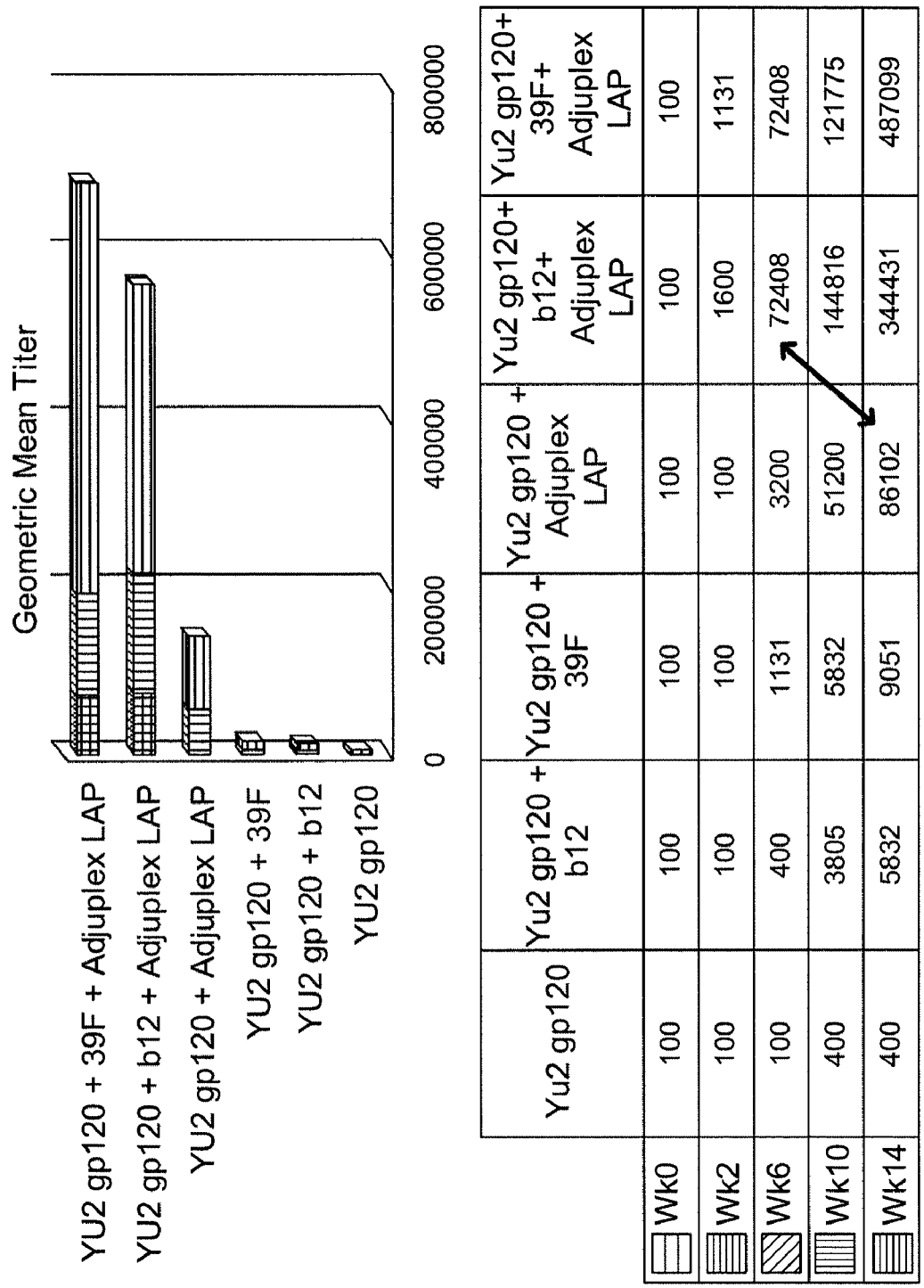
FIG. 5 depicts a mean titer: anti-env gp 120 response, specifically an ELISA anti-gp 120 titer in bleeds collected from rabbits 2 weeks post immunization by Yu2 gp 120 and the immune complex groups at weeks 2, 6, 10 and 14.
Figure 6:
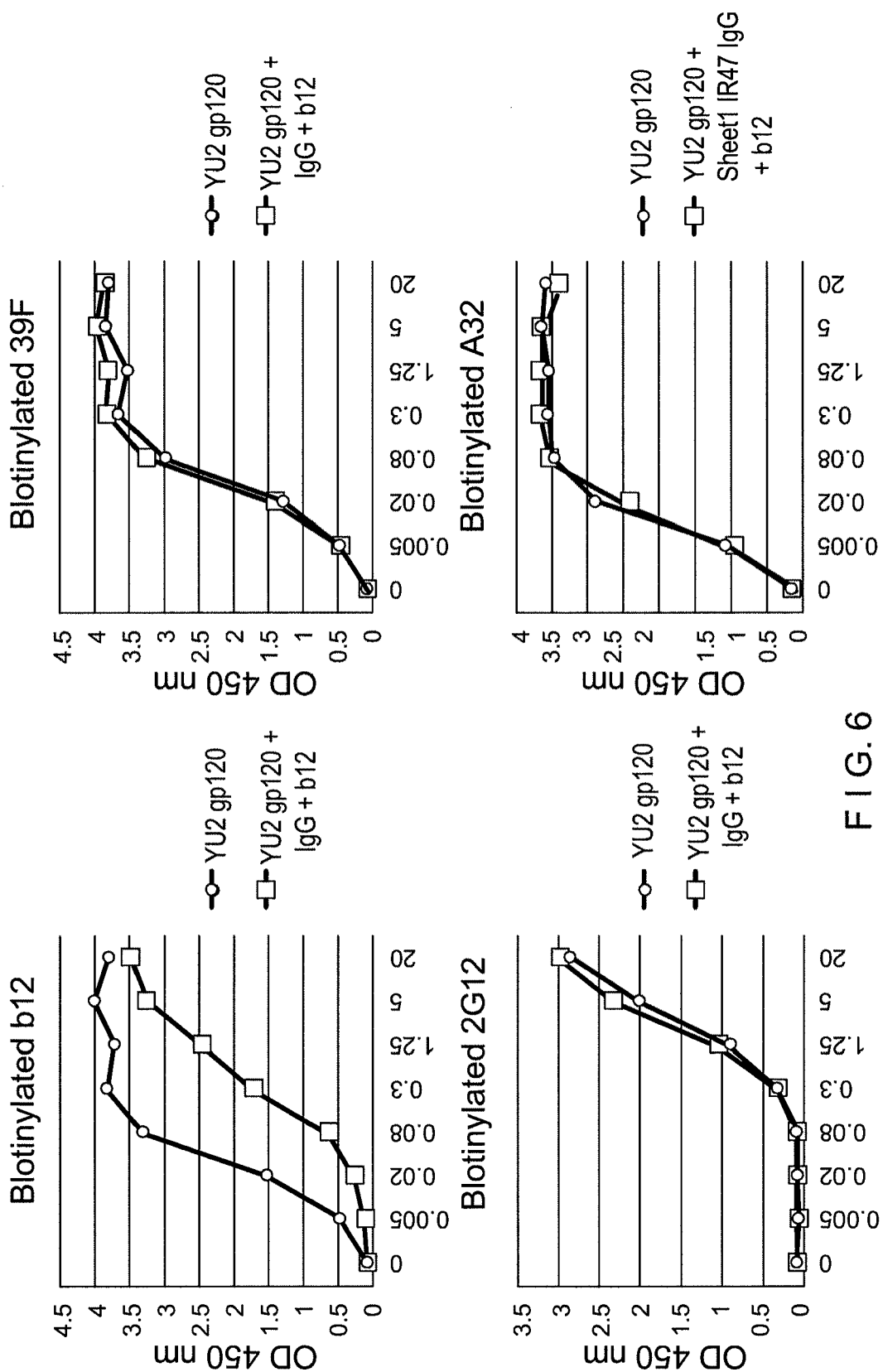
FIG. 6 depicts Yu2 gp 120 and Yu2gp 120-IgG b12 immune complexes captured on the ELISA plate which were probed with biotinylated conformational anti-HIV antibodies [b12 (binds CD4 binding site), 39F (binds V3 loop), 2G12 (recognizes glycan on the surface) and A32 (recognizes epitope on C1 and C5 region of YU2 gp 120)]. Except for IgG b12 site which is occupied in the immune complex all the other antibodies showed comparable binding to both Yu2 gp 120 and YU2 gp 120-IgG b12 immune complex.
Figure 7A:
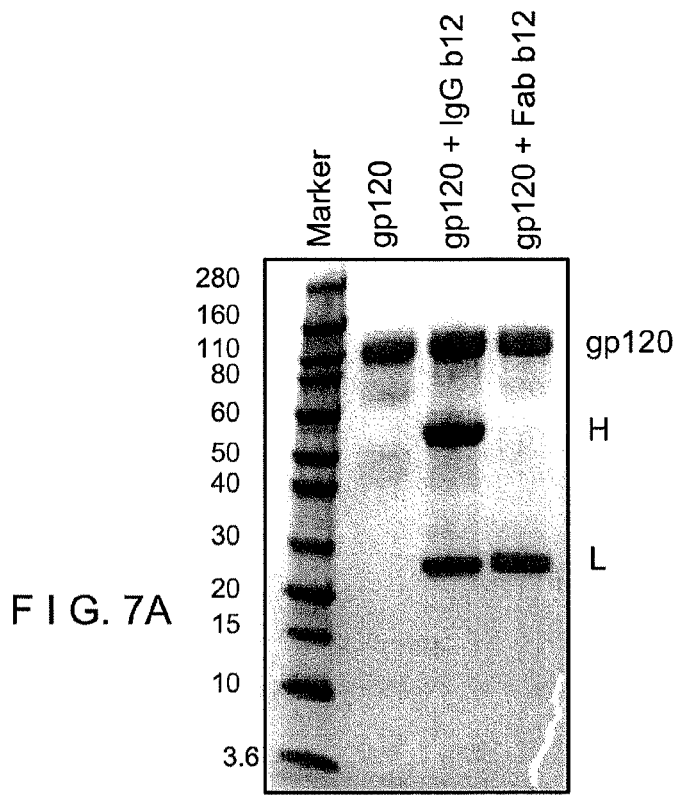
FIGS. 7A and 7B depicts generation of YU2 gp 120 immuen complex with Fab and IgG b12 (left) and anti-gp 120 titer in rabbits for the two immune complex group at weeks 6, 10 and 14. To determine the role of Fc, Yu2 gp 120 with Fab b 12 and IgG b12 immune complexes were generated and characterized (run and coommassie stained FIG. 7A). When immunized in rabbits the IgG b12 immune complex faired better in eliciting anti-gp 120 titer (graph in 7B) than the Fab b12 immune complex. At week 6 and week 10 (post 2 and 3 boost respectively) there was a 2-4 fold difference in titer. At week 10 both the groups had similar titer suggesting other factors like stabilization of the env, increase in size, besides the ability of FC to present to the antigen presenting cells.
Figure 7B:
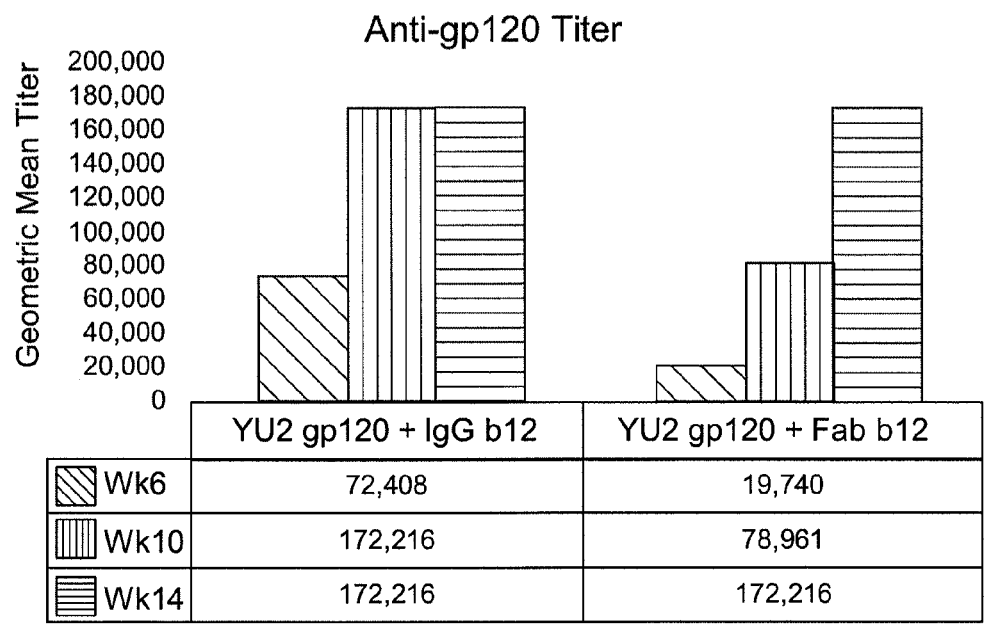
Figure 8:
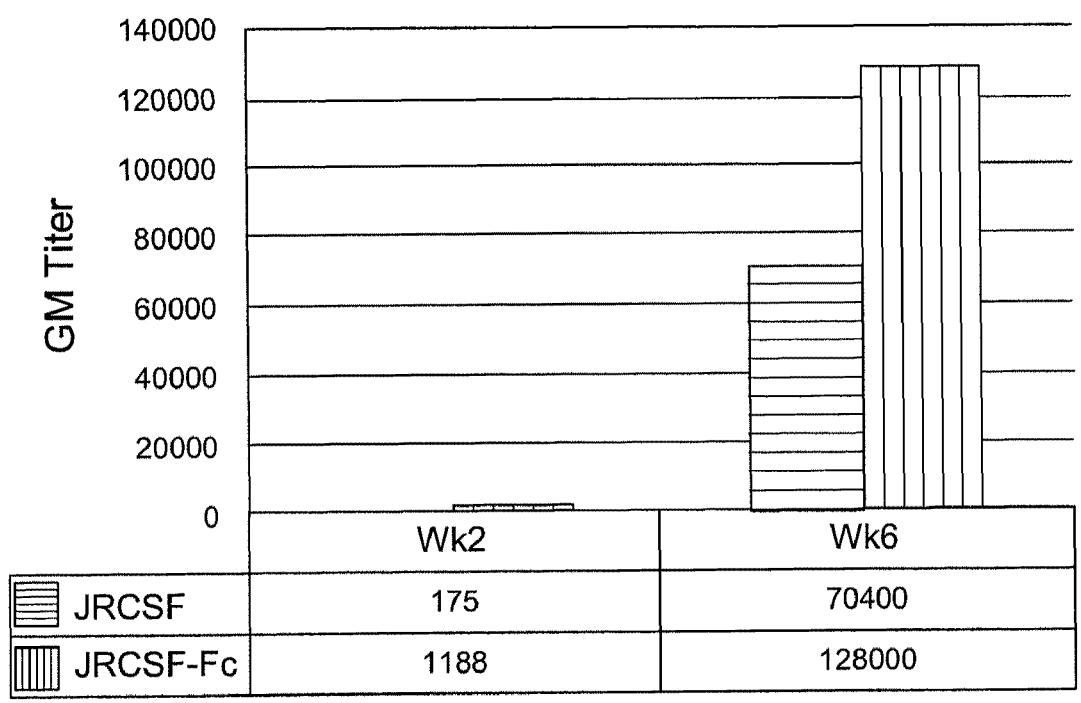
FIG. 8 depicts ELISA anti-gp 120 titer for JRCSF gp 10 and JRCSF-gp 120-Fc fusion protein (see, e.g., Binley J M et al., Inhibition of HIV Env binding to cellular receptors by monoclonal antibody 2G12 as probed by Fc-tagged gp 120, Retrovirology. 2006 July 3;3:39 and Retrovirology. 2007;4:23) at weeks 2 and 6.
Figure 9:
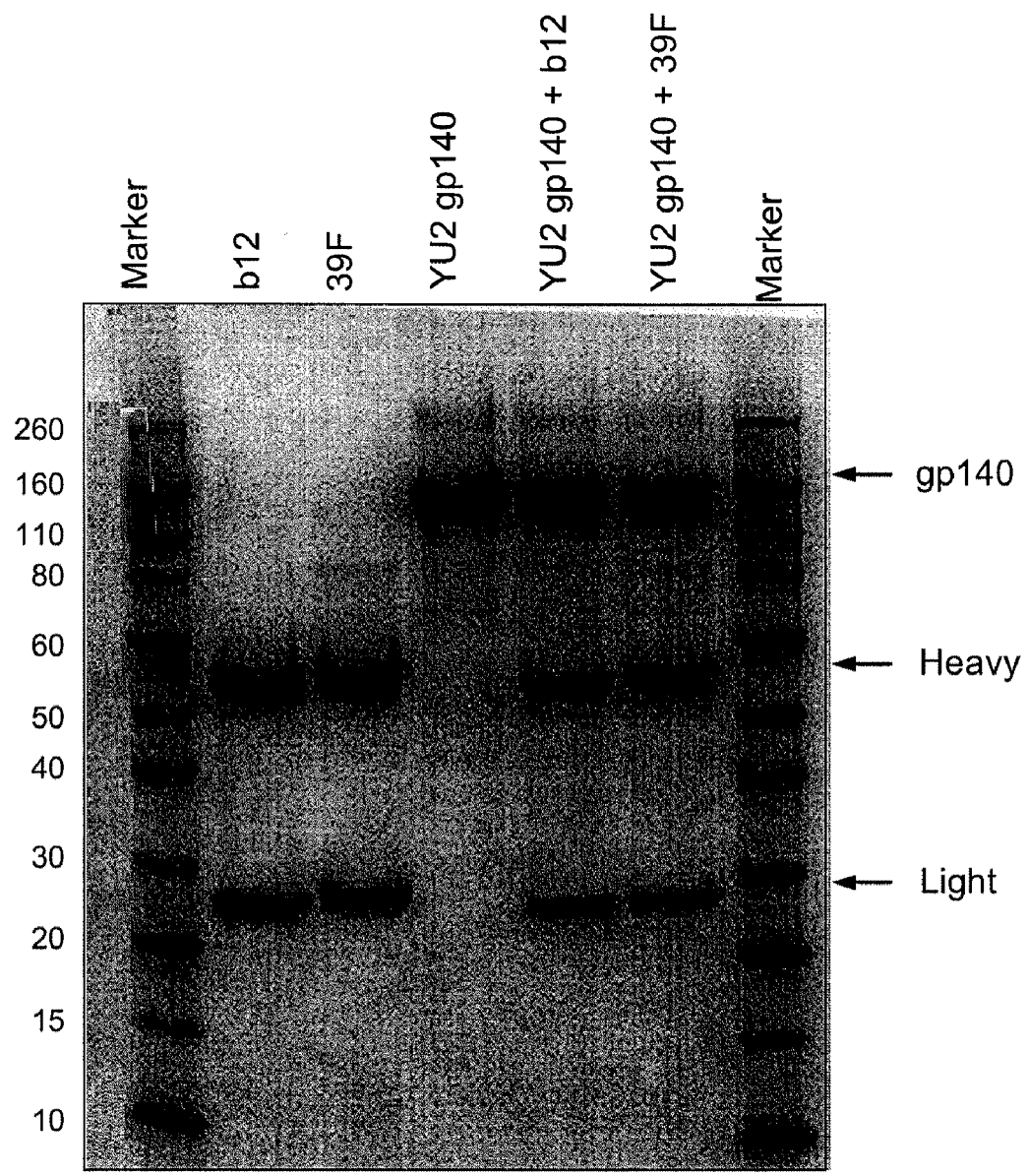
FIG. 9 depicts gel-filtration purified YU2 gp 140 immune complexes where lane 1 is marker, lane 2 is IgG b12, lane 3 is IgG 39F, lane 4 is YU2 gp 140, lane 5 is YU2 gp 140+IgG b12, lane 6 is YU2 gp 140+39F and lane 7 is marker.

The present invention relates to vaccines for HIV comprising antibody-antigen complexes. The current invention is based, in part, on Applicant's surprising discovery that immunization with antigen-antibody complexes elicit neutralizing antibody responses.

Previous attempts to elicit an effective neutralizing response from antigen-antibody complexes have failed, in particular an Env gp 120-antibody A32 complex (see, e.g., Liao et al., J Virol. 2004 May;78(10):5270-8).

The present invention encompasses identification of antibody-antigen complexes for use as a HIV vaccine. In one embodiment, the invention relates to the identification of immunogenic antibody-antigen complexes.

In an advantageous embodiment, the antigen-antibody complex is an envelope protein (such as, but not limited to, gp 120, gp 140 or membrane-associated envelope trimers) complexed with a CD4 binding site broad neutralizing antibody (such as, but not limited to, b12, 2F5), a variable loop 3 specific antibody (such as, but not limited to, 39F), a trimer-specific antibody (such as, but not limited to 2909, if the antigen is a envelope trimer protein) or a CD4 induced epitope specific antibody.

The invention encompasses mixing HIV antibodies, such as but not limited to, polyclonal anti-HIV sera, broadly neutralizing HIV monoclonal antibodies such as, but not limited to, b12, 2F5, 2G12, 4E10, M2909 either alone or combination or novel broadly neutralizing antibodies to HIV with purified HIV to enables the antibodies to bind to HIV antigens, such as but not limited to, the glycoprotein spikes on the viral envelopes, to form antibody-antigen complexes.

In an advantageous embodiment, the antigen-antibody complex comprises any form of HIV envelope glycoprotein or derivative thereof and any anti-HIV antibody or derivative thereof. The antigen-antibody complex advantageously improves the immunogenic response of an existing antigen.

The antigen-antibody complex of the present invention may potentiate an immune response via Fc receptor activity, increase germinal center formation to increase production of neutralizing antibodies, expose cryptic epitope on the immunogen due to better presentation of the antigen or protect and present a known epitope for neutralization (such as an antigen-antibody complex comprising neutralizing antibody b12).

Any HIV antigen may be used to form antibody-antigen complexes. Advantageously, the HIV antigen is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772;

6,030,770; 6,030,618; 6,025,141; 6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In a particularly advantageous embodiment, the HIV antigen is a peptide immunogen, such as but not limited to, 4E10 or 2F5. The peptide immunogen may comprise a tag, such as but not limited to, an HA tag or a sequence from the C5 region of HIV g120. Antibodies against the tag may be used to make the antigen-antibody complex to present the epitope to the immune system.

In another embodiment, HIV, or immunogenic fragments thereof, may be utilized as the HIV antigen may be used to form antibody-antigen complexes. For example, the HIV nucleotides of U.S. Pat. Nos. 7,393,949, 7,374,877,, 7,306, 901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any HIV antibody may be used to form antibody-antigen complexes. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

In another embodiment, the antibody-antigen complexes may be identified from alternate viral isolates, such as different HIV clades (see, e.g., U.S. Provisional Patent Application No. 60/810,816, filed Jun. 2, 2006, the disclosure of which is incorporated by reference). In this embodiment, polyclonal anti-HIV sera, broadly neutralizing HIV monoclonal antibodies such as, but not limited to, b12, 2F5, 2G12, 4E10, M2909 either alone or combination, or newly identified broadly neutralizing antibodies to HIV are mixed with different HIV clade viral isolates to enable the antibodies to bind to varying antigens, thereby forming antibody-antigen complexes.

The antibody-antigen complexes are dissociated, advantageously chemically dissociated, preferably by solubilizing the HIV lipid bilayer, from the virus. In another embodiment, the antibody-antigen complexes may be dissociated with an affinity column, such as, but not limited to, Clq, Protein A or Protein G affinity columns or secondary antibodies.

Gel filtration is advantageously used to purify antibody-antigen complexes in the present invention. Gel filtration is well known in the art and methods of U.S. Pat. Nos. 7,320,893; 7,276,355; 7,101,695; 7,098,026; 6,921,813; 6,812,015; 6,774,220; 6,753,185; 6,627,194; 6,613,564; 6,607,878; 6,600,022; 6,559,298; 6,541,217; 6,395,469; 6,352,723; 6,303,361; 6,274,709; 6,232,089; 6,210,708; 6,207,464; 6,197,297; 6,180,360; 6,156,519; 6,143,875; 6,103,234; 6,060,283; 6,025,165; 5,976,820; 5,942,411; 5,932,705; 5,932,700; 5,912,324; 5,871,936; 5,869,053; 5,856,113; 5,821,061; 5,817,769; 5,807,711; 5,798,445; 5,780,247; 5,721,342; 5,717,074; 5,707,819; 5,696,238; 5,665,864; 5,631,221; 5,629,165; 5,614,612; 5,606,027; 5,599,708; 5,583,199; 5,545,530; 5,523,210; 5,503,828; 5,502,163; 5,496,802; 5,436,319; 5,436,154; 5,338,832; 5,336,491; 5,324,822; 5,284,749; 5,258,324; 5,250,297; 5,234,911; 5,229,110; 5,208,021; 5,200,344; 5,151,266; 5,091,511; 5,089,262; 5,082,928; 5,071,759; 5,068,178; 5,047,503; 5,047,324; 5,037,958; 5,021,560; 5,000,953; RE33,405; 4,962,187; 4,959,320; 4,945,086; 4,916,055; 4,870,162; 4,843,004; 4,833,074; 4,814,433; 4,742,000; 4,686,284; 4,681,761; 4,661,348; 4,594,244; 4,544,640; 4,537,712; 4,532,207; 4,514,506; 4,514,505; 4,489,158; 4,476,093; 4,468,457; 4,446,240; 4,446,122; 4,431,582; 4,414,336; 4,343,734; 4,297,274; 4,232,001; 4,223,002; 4,195,073; 4,160,023; 4,132,769; 4,123,427 and 4,065,445 may be useful for the present invention.

To purify antibody-antigen complexes, Protein A, Protein G, precipitating secondary antibodies or Protein A-bearing *S. aureus* cells may be used. The affinity of an antibody for Protein A or G is dependent on the subclass of the immunoglobulin and the species from which it comes. For example, Protein A is exceptionally well suited for immunoprecipitation of all rabbit primary antibodies, but not for chicken antibodies. To use Protein A for immunoprecipitation of mouse primary antibodies, it is advisable to add 5 μg of rabbit anti-mouse IgG (secondary precipitating antibody) prior to the addition of Protein A/G (mix gently, and incubate for an additional 30 minutes at 4° C. prior to adding Protein A/G). Following addition of Protein A/G agarose, incubate with gentle agitation for 30 minutes at 4° C., then wash at least three times by centrifugation and resuspension in immunoprecipitation buffer and collect antibody-antigen-Protein A/G complexes by centrifugation. The purified immune complex may be used for immunizations or other immunochemical techniques.

Antibody-antigen complexes as vaccine formulations are known in the art and the disclosures of any one of Akagaki & Inai (1983) Mol Immunol 20(11): 1221-6, Alber et al. (2000) Vaccine 19(7-8): 895-901, Andersson et al. (1995) Scand J Immunol 42(4): 407-17, Barr et al. (2003) Immunology 109 (1): 87-92, Berger et al. (1996) Res Virol 147(2-3): 103-8, Berlyn et al. (2001) Clin Immunol 101(3): 276-83, Bonneau et al. (1972) Prog Immunobiol Stand 5: 537-41, Bouige et al. (1996) FEMS Immunol Med Microbiol 13(1): 71-9, Cannat et al. (1983) Ann Immunol (Paris) 134C(1): 43-53, Cavacini et al. (1995) J Immunol 155(7): 3638-44, Celis et al. (1987) Hepatology 7(3): 563-8, Chargelegue et al. (2005) Infect Immun 73(9): 5915-22, Dekker et al. (2004) Mol Biochem Parasitol 137(1): 143-9, Fenner (1972) Adv Exp Med Biol 31(0): 7-17, Genin & Lesavre (1983) Mol Immunol 20(10): 1069-72, Gnjatic et al. (2002) Proc Natl Acad Sci USA 99(18): 11813-8, Guo et al. (2004) Avian Dis 48(1): 224-8, Habig et al. (1988) J Pediatr 112(1): 162-3, Haddad et al. (1997) Avian Dis 41(4): 882-9, Hanke et al. (1992) J Gen Virol 73 (Pt 3): 653-60, Hsueh et al. (1997) Cancer J Sci Am 3(6): 364-70, Ivan et al. (2001) Vet Immunol Immunopathol 79(3-4): 235-48, Ivan et al. (2005) Can J Vet Res 69(2): 135-42, Jeurissen et al. (1998) Immunology 95(3): 494-500, Kostiala & Kosunen (1972) Scand J Immunol 1(2): 143-51, Kraiselburd (1987) P R Health Sci J 6(1): 27-9, Kraiselburd et al. (1981) Infect Immun 33(2): 389-94, Kurul et al. (2004) Pediatr Nephrol 19(6): 621-6, Li et al. (2004) BMC Neurosci 5: 21, Lurhuma et al. (1994) East Afr Med J 71(8): 493-5, Marques et al. (2005) Clin Diagn Lab Immunol 12(9): 1036-40, McCluskie et al. (1998) Viral Immunol 11(4): 245-52, Montefiori et al. (1994) J Infect Dis 170(2): 429-32, Navol'nev (1983) Vestn Dermatol Venerol (11): 23-7, O'Lee et al. (1987) Arch Oral Biol 32(8): 539-43, Paccaud et al. (1987) Clin Exp Immunol 69(2): 468-76, Parish (1972) Immunology 22(6): 1087-98, Pizarro et al. (2002) Acta Crystallogr D Biol Crystallogr 58(Pt 7): 1246-8, Pokric et al. (1993) Vaccine 11(6): 655-9, Polack et al. (2002) J Exp Med 196(6): 859-65, Rafiq et al. (2002) J Clin Invest 110(1): 71-9, Randall et al. (1993) Vaccine 11(12): 1247-52, Randall et al. (1994) Vaccine 12(4): 351-8, Randall & Young (1988) J Gen Virol 69 (Pt 10): 2505-16, Randall & Young (1989) J Virol 63(4): 1808-10, Randall et al. (1988) J Gen Virol 69 (Pt 10): 2517-26, Ridley et al. (1982) J Pathol 136(1): 59-72, Roic et al. (2006) J Vet Med B Infect Dis Vet Public Health 53(1): 17-23, Root-Bernstein (2004) J Clin Virol 31 Suppl 1: S16-25, Schifferli et al. (1988) J Immunol 140(3): 899-904, Schnurr et al. (2005) Blood 105(6): 2465-72, Schultes & Nicodemus (2004) Expert Opin Biol Ther 4(8): 1265-84, Schuurhuis et al. (2006) J Immunol 176(8): 4573-80, Semkow & Wilczynski (1979) Acta Virol 23(1): 52-8, Speranskaia et al. (1998) Zh Mikrobiol Epidemiol Immunobiol (2): 14-8, Stager et al. (2003) Nat Med 9(10): 1287-92, Stoner et al. (1975) J Infect Dis 131(3): 230-8, Trkola et al. (1995) J Virol 69(11): 6609-17, van Rooijen (1975) Immunology 28(6): 1155-63, Wen et al. (1994) Chin Med J (Engl) 107(10): 741-4, Wen et al. (1999) Int Rev Immunol 18(3): 251-8, Wen et al. (1995) Lancet 345(8964): 1575-6, Whipple et al. (2006) Mol Immunol. 2006 Apr 20; [Epub ahead of print]; Wyss-Coray et al. (1992) Cell Immunol 139(1): 268-73, Yoshikawa et al. (2004) J Gen Virol 85(Pt 8): 2339-46 and Zheng et al. (2001) Vaccine 19(30): 4219-25 may be utilized for methods of the present invention.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitopic determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the heavy chain; two Fab' fragments are obtained per antibody molecule;

(iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as -. Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993;90: 5873-5877.

Another example of a mathematical algorithm used for comparison of sequences is the algorithm of Myers & Miller, CABIOS 1988;4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993;Nature Genetics 3: 266-272; Karlin & Altschul, 1993;Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the antigens and/or antibodies of the invention can be expressed.

For example, when the aim 1s to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim 1s to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to selelct a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

In particularly preferred embodiments adenovirus vectors are used. Many adenovirus vectors are known in the art and any such suitable vector my be used. In preferred embodiments the adenovirus vector used is selected from the group consisting of the Ad5, Ad35, Ad11, C6, and C7 vectors.

The sequence of the Adenovirus 5 ("Ad5") genome has been published. (Chroboczek, J., Bieber, F., and Jacrot, B. (1992) The Sequence of the Genome of Adenovirus Type 5 and Its Comparison with the Genome of Adenovirus Type 2, Virology 186, 280-285; the contents if which is hereby incorporated by reference). Ad35 vectors are described in U.S. Pat. Nos. 6,974,695, 6,913,922, and 6,869,794. Ad11 vectors are described in U.S. Pat. No. 6,913,922. C6 adenovirus vectors are described in U.S. Pat. Nos. 6,780,407; 6,537,594; 6,309,647; 6,265,189; 6,156,567; 6,090,393; 5,942,235 and 5,833,975. C7 vectors are described in U.S. Pat. No. 6,277,558.

Adenovirus vectors that are E1-defective or deleted, E3-defective or deleted, and/or E4-defective or deleted may also be used. Certain adenoviruses having mutations in the E1 region have improved safety margin because EI-defective adenovirus mutants are replication-defective in non-permissive cells, or, at the very least, are highly attenuated. Adenoviruses having mutations in the E3 region may have enhanced the immunogenicity by disrupting the mechanism whereby adenovirus down-regulates MHC class I molecules. Adenoviruses having E4 mutations may have reduced immunogenicity of the adenovirus vector because of suppression of late gene expression. Such vectors may be particularly useful when repeated re-vaccination utilizing the same vector is desired. Adenovirus vectors that are deleted or mutated in E1, E3, E4, E1 and E3, and E1 and E4 can be used in accordance with the present invention.

Furthermore, "gutless" adenovirus vectors, in which all viral genes are deleted, can also be used in accordance with the present invention. Such vectors require a helper virus for their replication and require a special human 293 cell line expressing both E1a and Cre, a condition that does not exist in natural environment. Such "gutless" vectors are non-immunogenic and thus the vectors may be inoculated multiple times for re-vaccination. The "gutless" adenovirus vectors can be used for insertion of heterologous inserts/genes such as the transgenes of the present invention, and can even be used for co-delivery of a large number of heterologous inserts/genes.

The nucleotide sequences and vectors of the invention can be delivered to cells, for example if aim 1s to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

Following expression, the antibodies and/or antigens of the invention can be isolated and/or purified or concentrated using any suitable technique known in the art. For example, anion or cation exchange chromatography, phosphocellulose chromatography, hydrophobic interaction chromatography, affinity chromatography, immuno-affinity chromatography, hydroxyapatite chromatography, lectin chromatography, molecular sieve chromatography, isoelectric focusing, gel electrophoresis, or any other suitable method or combination of methods can be used.

In preferred embodiments, the nucleotide sequences, antibodies and/or antigens of the invention are administered in vivo, for example where the aim 1s to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO$_4$)$_2$, AlNa(SO$_4$)$_2$, AlNH(SO$_4$)$_2$, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, such as those described in Chuang, T.H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC3 1; see Schellack, C. et al (2003) Proceedings of the 34$^{th}$ Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057, 540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689, 338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the antibodies, antigens, antibody-antigen complexes, nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulations can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly- (methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the antibodies, antigens, antibody-antigen complexes, nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratry animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

Previous attempts to elicit an effective neutralizing response from antigen-antibody complexes have failed, in particular an Env gp 120-antibody A32 complex (see, e.g., Liao et al., J Virol. 2004 May;78(10):5270-8). One hypothesis as to the failure is the high dose of env (100 to 200 µg) in the gp 12-32 complex. Advantageously, a lower dose of env is contemplated, such as about 1 µg to about 50 µg, about 2.5 µg to about 40 µg, about 5 µg to about 30 µg, about 7.5 µg to about 20 µg, preferably about 10 µg to about 15 µg of env when env is the antigen in the antigen-antibody complex.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, especially DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the antibodies, antigens, antibody-antigen complexes of the invention, one or more times to a subject wherein the antibodies, antigens, antibody-antigen complexes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an antibody, antigen or antibody-antigen complex of the present invention, a nucleic acid encoding an antibody, antigen or antibody-antigen complex of the invention or an expression vector, preferably an adenovirus vector, encoding an antibody, antigen or antibody-antigen complex of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

It is to be understood and expected that variations in the principles of invention as described above may be made by one skilled in the art and it is intended that such modifications, changes, and substitutions are to be included within the scope of the present invention.

The invention will now be further described by way of the following non-limiting examples.

EXAMPLE

HIV Envelope Immune Complexes as a Vaccine Candidate

Immune complexes (ICs) of protein antigen and specific antibodies can markedly enhance the immunogenicity of the antigen (Roosnek and Lanzavecchia J Exp Med 173:487-489) by presumably providing the adjuvant effect and better presentation of the antigen to the antigen presenting cells.

The advantages of immune complexes include, but are not limited to:

1. Immune complexes are efficiently taken up by specialized antigen-presenting cells (dendritic cells (DC)) via Fc receptors,
2. Binding of ICs to Fc receptors can mediate dendritic cell maturation serving as a natural adjuvant,
3. Immune complex increase the germinal center formation and thus could effect the quality of antibody formation,
4. Antibody binding to the antigen could potentially present the cryptic epitopes by masking the immunodominant epitopes and
5. Alteration of proteolysis of the antigen by formation of the immune complex could alter the presentation to CD4 T-cell, In the veterinary immune complex vaccine follicular dendritic cells and B-lymphocytes were rescued from depletion either by protection of the lymphocyte against the lytic effect of the virus or by maintaining a more intact microenvironment needed by FDC. The veterinary immune complex vaccine also induced formation of germinal centers containing the Immune complex in spleen. Immunization with Immune complexes accelerated the development of memory B-cells and affinity maturation of antibodies compared to antigen alone. The repertoire of antigen reactive B-cells in immune complex immunization showed presence of heterogenous VH gene expression while in antigen alone immunization only single variable gene was observed.

Initially gp 120 and gp 120 complexes were tested with one broad neutralizing antibody b12 and one non neutralizing antibody 39F. This line of experimentation helps determine the baseline activity upon immunization.

The experimental steps were as follows:

1. Determining YU2 gp 120 run profile through a gel filtration chromatography,
2. Making Yu2gp 120 and monoclonal antibody complexes and purify on Ag—Ab complex by gel filtration,
3. Characterizing the stochiometry of Ag—Ab by blue native and denaturing PAGE,
4. Immunizing rabbits intramuscularly with gp 120 and gp 120-Ab complexes at 13 ug Env dose with adjuplex adjuvant and
5. Evaluating the sera for binding and neutralization assay.

The present study was performed with immune complexes of HIV envelope YU2 gp 120 and antibodies b12, a CD4 binding site broad neutralizing antibody and 39F, a variable loop 3 specific antibody on gp 120.

The rationale for using b12 antibody to make Yu2gp 120-b12 immune complex was:

1. B12 Immune complexes would be efficiently taken up by specialized antigen-presenting cells (dendritic cells (DC)) via Fc receptors.
2. B12 antibody binding region is crucial for the viral entry and preservation of this site by making a complex with the antibody is desirable and
3. Binding of b12 to gp 120 does not lead to major conformational changes as measured by isothermal calorimetry potentially allowing stabilization of the Env gp 120 in one fixed state. Env gp 120 is highly flexible molecule and fixing in one state is presumed to be better for the immunogenic property.

The binding of Fc receptor but not complement to antibody b12 was shown to be important for anti-HIV activity.

The rationale for using 39F antibody to make Yu2gp 120-b12 immune complex was:

1. 39F Immune complexes would be efficiently taken up by specialized antigen-presenting cells (dendritic cells (DC)) via Fc receptors,
2. 39F antibody binding region (Variable loop 3) is immunidominant, masking of the immunodominant and strain specific epitope and would support the presentation of cryptic or immunosilent epitope and 3. Binding of 39F to gp 120 potentially allows stabilization of the Env gp 120 in one fixed state. Env gp 120 is highly flexible molecule and fixing in one state is presumed to be better for the immunogenic property.

TABLE 1

Soluble gp120 YU2 complexes

| Antigen | Antibody | Binding |
|---------|----------|---------|
| YU2 gp120 | 39F | Binds V3 loop |
| YU2 gp120 | b12 | CD4 Binding Site |

Yu2 gp 120+b12 and Yu2 gp 120+39F immune complexes were generated and purified at a molar ratio of 1:1 Env to antibody molecules pushed all the envelope molecules into complex formation (FIG. 1). The immune complexes were stable when stored at 4C for days and at −70C for days. The b12 immune complexes were of one type 1:1 of gp 120-b12 molecule, where as the 39F immune complexes showed presence of two forms presumably 1:1 and 1:2 of gp 120-39F molecules (FIG. 2). The immune complexes were analyzed on reducing PAGE for stochiometry and purity and equal amounts of Env (gp 120) and antibody (heavy and light chains) were observed (FIG. 3). Approximately 10-15 ug of gp 120 equivalent of Env or Env-Ab Immune complexes were immunized in rabbits at 0, 4, 8 and 12 weeks with and with out adjuvant Adjuplex LAP. Bleeds were collected at 2, 6, 10 and 14 weeks and analyzed by ELISA and neutralization assay. After a single priming the immune complex group with adjuvant showed formation of anti-Env antibodies at a titer of 6400 (FIG. 4). Following one prime and one boost anti-Env titer reached 105 for most animals in the immune complex group with adjuvant whereas all other groups had very low titer antibodies. These sera were further tested for neutralization ability against 10 different HIV-1 isolates. The env alone group with adjuvant showed low titer neutralization of easy to neutralize SF162 and NL4-3 viruses, whereas the immune complex group with showed neutralization of good neutralization Bal, BX08, SF162 and NL4-3, a few animals in the immune complex group also neutralized HT593, JRCSF and BR020 viruses.

The use of adjuvant adjuplex helped the immune complex group significant as is seen by comparing the immune complex with and with out adjuvant group. This adjuvant helps generation of high titer ELISA antibodies in quick and durable fashion as has been seen in case of Env gp 140 and env gp 120. Env alone group with adjuplex showed generation of good titer anti-Env antibodies only after one prime and two or three boost but showed neutralizing antibodies only against SF162 and NL4-3, suggesting the importance of immune complex in generating high titer neutralizing antibodies with breadth of neutralization.

Experiments with Soluble HIV Env Trimer. The data and assay conditions so obtained from the above experiment are used generate Ag—Ab complexes with HIV Env soluble gp 140 molecules. For soluble HIV-1 gp 140 molecules, broad neutralizing antibodies b12 and 2F5 and non neutralizing antibody 39F directed to variable loop 3 on gp 120 are used.

Experimental steps include:

1. Determining YU2 gp 140 or JRCSF gp 140 run profile through a gel filtration chromatography, 2. Making Yu2/JRCSF gp 140 and monoclonal antibody complexes and purify on Ag—Ab complex by gel filtration, 3. Characterizing the stochiometry of Ag—Ab by blue native and denaturing PAGE, 4. Immunizing rabbits intramuscularly with gp 140 and gp 140-Ab complexes at different dose with adjuplex adjuvant and 5. Evaluating the sera for binding and neutralization assay.

Experiment with Membrane Associated Envelope Trimer. HIV-1 virion treated with aldrithiol-2 inactivates the virus by covalently modifying the essential zinc finger motifs in the nucleocapsid protein (NC7). Interestingly, such AT-2 inactivated viruses preserve the conformational integrity of the virion surface proteins. The functional viral spike is membrane associated and presumably the best trimer; in this regard, inactivated HIV-1 virion is used to make membrane associated trimer to form ICs with 2909 (trimer specific), b12 (CD4 Binding site) and V3 specific antibodies.

A low dose of Env is important as immune complexes have various regulatory functions and a high dose of Env may lead to immunopathogenesis.

Biophysical Characterization of Immune Complexes as HIV-1 Vaccine Candidate. A protective vaccine against HIV-1 remains elusive and the conventional methods of live attenuated or inactivated virus vaccine raise significant safety concerns. Subunit vaccines containing HIV-1 envelope glycoprotein elicit neutralizing antibodies limited to the virus strains from which the immunogen is designed and is thus inadequate as a vaccine candidate. Immune complexes may be utilized as a candidate HIV vaccine immunogen. Soluble YU2 gp 120 (Clade B Envelope protein) complexed with b12, a broadly neutralizing antibody against the CD4 binding site, and separately with 39F, a non-neutralizing antibody against the immunodominant V3 loop were generated. The complexes were purified by size exclusion chromatography on Superdex 200 column and characterized by SDS PAGE and dynamic light scattering. To determine the size of the complexes and individual components, size exclusion chromatography on Superose 12 column coupled to AKTA UV detector, miniDawn Treos with WyattQELS and OptiLab rEX was used. All parameters were calculated by using Astra 5.3.2 software. For highly glycosylated HIV Envelope proteins, a three-detector method was used. Serum from rabbits immunized with ICs contained significant anti-Envelope binding and neutralizing antibody titers. Suboptimal concentrations of the envelope in the immune complex elicited significant neutralizing antibody responses against a panel of clad B HIV viruses tested. Immune complexes evoked neutralizing activity significantly more potent than the control envelope alone group which was mapped to the variable loop 3 of the HIV envelope glycoprotein. On-going studies may determine the role of the Fcγ portion of antibody and the size of the complex in the immune potentiation.

SF 162 Neutralization Titer: $IC_{50\ and\ 90}$ Values. Neutralization $IC_{50}$ and $IC_{90}$ values of immune complex derived rabbit sera against HIV-1 clade B SF162 virus. As shown in Table 2, Immune complex group sera has significant $IC_{90}$ titer against SF162 following a single prime and boost immunization.

TABLE 2

SF162 Neutralization Titer: IC50 and 90 Values

Without Adjuvant

| | | IC50 | IC90 |
|---|---|---|---|
| | Wk0 | <10 | <10 |
| | Wk2 | <10 | <10 |
| | WK6 | <10 | <10 |
| | Wk10 | <10 | <10 |
| | Wk14 | <10 | <10 |
| | Wk0 | <10 | <10 |
| | Wk2 | <10 | <10 |
| | WK6 | | <10 |
| | Wk10 | 20-209 | |
| | Wk14 | 15-165 | |
| | Wk0 | <10 | <10 |
| | Wk2 | <10 | <10 |
| | WK6 | | <10 |
| | Wk10 | | <10 |
| | Wk14 | 19-51 | <10 |

TABLE 2-continued

SF162 Neutralization Titer: IC50 and 90 Values

With Adjuvant

| | | IC50 | IC90 |
|---|---|---|---|
| | Wk0 | <10 | <10 |
| | Wk2 | <10 | <10 |
| | WK6 | | <10 |
| | Wk10 | 28-110 | <10 |
| | Wk14 | | |
| | Wk0 | <10 | <10 |
| | Wk2 | | |
| | WK6 | 26-1748 | 11-268 |
| | Wk10 | 295-2824 | 58-469 |
| | Wk14 | 77-1016 | 12-246 |
| | Wk0 | <10 | <10 |
| | Wk2 | <10 | <10 |
| | WK6 | 136-469 | |
| | Wk10 | 144-757 | |
| | Wk14 | 201-633 | |

Responding animals    2/4

Rabbit Sera Neutralization: IC$_{50}$ Value. Table 3 depicts neutralization IC$_{50}$ value of immune complex derived rabbit sera against a panel of 10 clade B HIV-1 viruses. Immune complex derived sera neutralizes six out of 10 viruses tested.

TABLE 3

Rabbit Sera Neutralization: IC50 value

| | | 1196 | BR020 | HT593 | US712 | Bal | BX08 | JRFL | SF162 | JRCSF | NL4-3 | aMLV |
|---|---|---|---|---|---|---|---|---|---|---|---|---|
| | Wk0 | <10 | <10 | <10 | <10 | <10 | <10 | <10 | <10 | <10 | <10 | <10 |
| | Wk2 | <10 | <10 | <10 | <10 | <10 | <10 | <10 | <10 | <10 | <10 | <10 |
| | WK6 | <10 | <10 | <10 | <10 | <10 | <10 | <10 | | <10 | 13-23 | <10 |
| | Wk10 | <10 | <10 | <10 | <10 | <10 | <10 | <10 | 28-110 | <10 | | <10 |
| | Wk14 | <10 | <10 | | <10 | | | <10 | | | | <10 |
| | Wk0 | <10 | <10 | <10 | <10 | <10 | <10 | <10 | <10 | <10 | <10 | <10 |
| | Wk2 | <10 | <10 | <10 | <10 | <10 | <10 | <10 | | <10 | <10 | <10 |
| | WK6 | <10 | <10 | <10 | <10 | 15-23 | | <10 | | <10 | | <10 |
| | Wk10 | <10 | <10 | <10 | <10 | | | <10 | | <10 | | <10 |
| | Wk14 | <10 | | | <10 | | | <10 | | <10 | | <10 |
| | Wk0 | <10 | <10 | <10 | <10 | <10 | <10 | <10 | <10 | <10 | <10 | <10 |
| | Wk2 | <10 | <10 | <10 | <10 | <10 | <10 | <10 | <10 | <10 | <10 | <10 |
| | WK6 | <10 | <10 | <10 | <10 | <10 | | <10 | <10 | <10 | | <10 |
| | Wk10 | <10 | <10 | <10 | <10 | | | <10 | | <10 | | <10 |
| | Wk14 | <10 | 14-18 | 12-22 | <10 | | | <10 | | <10 | | <10 |
| | | | | | | | | | | | | <50 |

Responding animals    2/4

Mapping of the Sera for Binding and Neutralizing Antibodies. Table 4 depicts the variable loop 3 sequence of al the viruses neutralized by immune complex rabbit sera.

TABLE 4

Mapping of the sera for binding and neutralizing antibodies
(SEQ ID NOS 1-7, respectively in order of appearance)

| | Virus | base/Stem/Tip/stem/base V3 Sequence |
|---|---|---|
| Immunogen | YU2 | CTRPNNNTRKSINI--GPGRALYTTGEIIGDIRQAHC |
| | SF162 | CTRPNNNTRKSITI--GPGRAFYATGGIIGDIRQAHC |
| | Bx08 | CTRPNNNTRKSIHI--GPGRAFYTTGDIIGDIRQAHC |
| | HT593 | CTRPNNNTSKRISI--GPGRAFRAT-KIIGNIRQAHC |
| | Bal | CTRPNNNTRKSIHI--GPGRALYTTGEIIGDIRQAHC |
| | BR020 | CTRPNNNTRKSIHI--GPGRAFYATGDIIGDIRQAHC |
| | NL4-3 | CTRPNNNTRKSIRIQRGPGRAFVTIGKI-GNMRQAHC |

YU2 V3 Peptide Absorption of Neutralizing Ability. Table 5 depicts absorption of neutralizaion activity by YU2 V3 peptide for a) anti-V3 monoclonal antibody 447-52D, b) a control human sera with broad neutralization specificity c) YU2 gp 120 generated rabbit sera and d) Immune complex generated sera.

TABLE 5

YU2 V3 Peptide Absorption of Neutralizing Ability a)

| Mab/Sera | Peptide | 92BR020 | 92HT593 | Bal | Bx08 | SF162 | JRCSF | NL4-3 | aMLV |
|---|---|---|---|---|---|---|---|---|---|
| 447-52D | No Peptide | | | | | 0.02 | | 116 | >50 |
| 447-52D | V3 peptide | | | | | >50 | | >50 | >50 | b)

| | | | | | | | | | |
|---|---|---|---|---|---|---|---|---|---|
| Z23 sera | No Peptide | 340 | 419 | 1153 | 1225 | 21406 | 438 | 4170 | <100 |
| Z23 sera | V3 peptide | 127 | 140 | 6 | 30 | 575 | 65 | 4075 | <10 | c)

| Group | Peptide | 92BR020 | 92HT593 | Bal | Bx08 | SF162 | JRCSF | NL4-3 | aMLV |
|---|---|---|---|---|---|---|---|---|---|
| Env | No Peptide | <10 | <10 | <10 | <10 | 101 | <10 | 116 | <10 |
| Env | V3 peptide | <10 | <10 | <10 | <10 | 105 | <10 | 91 | <10 | d)

| Env+Ab | No Peptide | 22 | 35 | 51 | 1225 | 1909 | 41 | 66 | <10 |
| Env+Ab | V3 peptide | <10 | 25 | <10 | 6 | 6 | <10 | 55 | <10 |

50 ug/ml V3 peptide added along with the sera and neutralization performed in a 10 point dilution curve to determine IC50 value Size of Yu2 gp 120 and Immune Complexes. Table 6 depicts the size (hydrodynamic radius) as measured by dynamic light scatter for Fab, IgG and Env immune complexes.

TABLE 6

Size of Yu2 gp120 and Immune complexes

| Protein or complex | Rh (nm) from SEC-QELS | Mw (kDa) | Rf (ml) of the major peak |
|---|---|---|---|
| b12 Fab | 3.8 | 50.7 | 15.5 |
| b12 | 5.5 | 146.6 | 13.0 |
| YU2 gp120 | 5.2 | 99.9 (55.6 + 44.3) | 12.6 |
| YU2 gp120 + b12 Fab | 6.1 | | 11.9 (complex) 15.5 (Fab) |
| YU2 gp120 + b12 IgG | 7.5 | | 10.2 |

Rh = Hydodynamic radius;
SEC-QELS Size exclusion Chromatography-Quasi Elastic Light scattering;
Mw: = Molecular weight;
Rf = retention factor.
Superose 12 10/30 column The invention is further described by the following numbered paragraphs:

1. A method of producing an immune response comprising administering to a mammal a purified antibody-antigen complex dissociated from polyclonal anti-HIV sera bound to glycoprotein spikes on HIV envelopes.

2. A method of producing an immune response comprising administering to a mammal a purified antibody-antigen complex dissociated from a mixture of broadly neutralizing antibodies and HIV, wherein the mixture is bound to glycoprotein spikes on HIV envelopes.

3. The method of paragraph 2 wherein the antibodies are monoclonal antibodies.

4. The method of paragraph 3 wherein the monoclonal antibodies are b12, 2F5, 2G12, 4E10, M2909 or any combination thereof.

5. The method of any one of paragraphs 2-4 wherein the HIV is purified HIV.

6. The method of any one of paragraphs 2-4 wherein the HIV is a HIV viral isolate.

7. The method of paragraph 6 wherein the HIV viral isolate is a HIV clade viral isolate.

8. The method of any one of paragraphs 1-7 wherein the purified antibody-antigen complex is chemically dissociated from the glycoprotein spikes.

9. The method of any one of paragraphs 1-8 wherein the purified antibody-antigen complex is dissociated from the glycoprotein spikes by solubilizing a HIV lipid bilayer.

10. The method of any one of paragraphs 1-7 wherein the purified antibody-antigen complex is purified with Protein A, protein G, precipitating secondary antibodies or Protein A-bearing *S. aureus* cells.

11. The method of any one of paragraphs 1-10 wherein the mammal is a human.

12. The method of any one of paragraphs 1-11 wherein the purified antibody-antigen complex is administered in a pharmaceutically acceptable carrier.

13. The method of any one of paragraphs 1-12 wherein the administering further comprises a prime-boost regimen.

14. A method of producing an immune response comprising administering to a mammal an antibody-antigen complex, wherein the antigen is an HIV envelope protein.

15. The method of paragraph 14 wherein the HIV envelope protein is gp 120, gp 140 or a membrane associated envelope trimer.

16. The method of any one of paragraphs 14-15 wherein the antibody is a broad neutralizing antibody.

17. The method of paragraph 16 wherein the broad neutralizing antibody is antibody b12.

18. The method of any one of paragraphs 14-15 wherein the antibody is a non-neutralizing antibody.

19. The method of paragraph 18 wherein the non-neutralizing antibody is a V3 specific antibody.

20. The method of paragraph 19 wherein the non-neutralizing antibody is antibody 39F.

21. The method of paragraph 15 wherein the HIV envelope protein is a membrane associated envelope trimer and the antibody is a trimer specific antibody 2909.

22. The method of any one of paragraphs 14-21 wherein the antibody-antigen complex is purified by gel filtration.

23. The method of any one of paragraphs 14-22 wherein the mammal is a human.

24. The method of any one of paragraphs 14-23 wherein the antibody-antigen complex is administered in a pharmaceutically acceptable carrier.

25. The method of any one of paragraphs 14-24 further comprising an adjuvant.

26. The method of paragraph 25 wherein the adjuvant is Adjuplex LAP.

27. The method of any one of paragraphs 14-26 wherein the dosage of the HIV envelope protein is about 10 µg to about 15 µg.

28. The method of any one of paragraphs 14-27 wherein the administering further comprises a prime-boost regimen.

29. The method of any one of paragraphs 14-28 wherein the antibody-antigen complex is expressed in a viral vector.

30. The method of paragraph 29 wherein the antibody-antigen complex is expressed in vivo.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of producing an anti-human immunodeficiency virus (HIV) neutralizing antibody response in a host comprising the following steps:
   1) isolating or purifying an immunogen comprising an antibody-antigen complex comprising a neutralizing monoclonal antibody (Mab) selected from the group consisting of Mab b12 or 39F and an HIV-1 soluble gp120 YU2 Env glycoprotein, 2) administering the immunogen of step 1) under conditions that produce the desired immune response, and 3) assaying for the presence of said neutralizing antibodies in said host.

2. The method of claim 1 wherein the antibody is Mab b12.

3. The method of claim 1 wherein the antibody is Mab 39F.

4. The method of claim 1 wherein the antibody is HIV-1 soluble gp120 YU2 Env glycoprotein.

5. The method of claim 1 wherein the purified antibody-antigen complex is administered in a pharmaceutically acceptable carrier.

6. The method of claim 1 wherein the administering further comprises a prime-boost regimen.

7. The method of claim 1 further comprising an adjuvant.

8. The method of claim 7 wherein the adjuvant is Adjuplex LAP.

* * * * *

```
SEQUENCE LISTING

<160> NUMBER OF SEQ ID NOS: 7

<210> SEQ ID NO 1
<211> LENGTH: 35
<212> TYPE: PRT
<213> ORGANISM: Human immunodeficiency virus

<400> SEQUENCE: 1

Cys Thr Arg Pro Asn Asn Asn Thr Arg Lys Ser Ile Asn Ile Gly Pro
1               5                   10                  15

Gly Arg Ala Leu Tyr Thr Thr Gly Glu Ile Ile Gly Asp Ile Arg Gln
            20                  25                  30

Ala His Cys
        35

<210> SEQ ID NO 2
<211> LENGTH: 35
<212> TYPE: PRT
<213> ORGANISM: Human immunodeficiency virus

<400> SEQUENCE: 2

Cys Thr Arg Pro Asn Asn Asn Thr Arg Lys Ser Ile Thr Ile Gly Pro
1               5                   10                  15

Gly Arg Ala Phe Tyr Ala Thr Gly Gly Ile Ile Gly Asp Ile Arg Gln
            20                  25                  30

Ala His Cys
        35

<210> SEQ ID NO 3
<211> LENGTH: 35
<212> TYPE: PRT
<213> ORGANISM: Human immunodeficiency virus

<400> SEQUENCE: 3

Cys Thr Arg Pro Asn Asn Asn Thr Arg Lys Ser Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35
```

```
<210> SEQ ID NO 4
<211> LENGTH: 34
<212> TYPE: PRT
<213> ORGANISM: Human immunodeficiency virus

<400> SEQUENCE: 4

Cys Thr Arg Pro Asn Asn Asn Thr Ser Lys Arg Ile Ser Ile Gly Pro
1               5                   10                  15

Gly Arg Ala Phe Arg Ala Thr Lys Ile Ile Gly Asn Ile Arg Gln Ala
            20                  25                  30

His Cys

<210> SEQ ID NO 5
<211> LENGTH: 35
<212> TYPE: PRT
<213> ORGANISM: Human immunodeficiency virus

<400> SEQUENCE: 5

Cys Thr Arg Pro Asn Asn Asn Thr Arg Lys Ser Ile His Ile Gly Pro
1               5                   10                  15

Gly Arg Ala Leu Tyr Thr Thr Gly Glu Ile Ile Gly Asp Ile Arg Gln
            20                  25                  30

Ala His Cys
        35

<210> SEQ ID NO 6
<211> LENGTH: 35
<212> TYPE: PRT
<213> ORGANISM: Human immunodeficiency virus

<400> SEQUENCE: 6

Cys Thr Arg Pro Asn Asn Asn Thr Arg Lys Ser Ile His Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

<210> SEQ ID NO 7
<211> LENGTH: 36
<212> TYPE: PRT
<213> ORGANISM: Human immunodeficiency virus

<400> SEQUENCE: 7

Cys Thr Arg Pro Asn Asn Asn Thr Arg Lys Ser Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35
```